(12) United States Patent
Drennan

(10) Patent No.: US 7,458,948 B2
(45) Date of Patent: Dec. 2, 2008

(54) HEEL-SUPPORTING PROTECTIVE BOOT

(76) Inventor: Denis Burke Drennan, 4 Milburn Park, Evanston, IL (US) 60201

( * ) Notice: Subject to any disclaimer, the term of this patent is extended or adjusted under 35 U.S.C. 154(b) by 461 days.

(21) Appl. No.: 11/162,842

(22) Filed: Sep. 26, 2005

(65) Prior Publication Data

US 2007/0073208 A1 Mar. 29, 2007

(51) Int. Cl.
*A61F 5/00* (2006.01)
(52) U.S. Cl. .............. 602/23; 602/27; 128/882
(58) Field of Classification Search .......... 602/3, 602/5, 23, 27–29; 128/845, 846, 878, 879, 128/881, 882
See application file for complete search history.

(56) References Cited

U.S. PATENT DOCUMENTS

| | | |
|---|---|---|
| 4,186,738 A | 2/1980 | Schleicher et al. .......... 128/153 |
| 5,367,789 A | 11/1994 | Lamont |
| 5,449,339 A | 9/1995 | Drennan ................ 602/23 |
| 5,735,805 A | 4/1998 | Wasserman et al. |

*Primary Examiner*—Michael A. Brown
(74) *Attorney, Agent, or Firm*—Hartman & Hartman, P.C.; Gary M. Hartman; Domenica N. S. Hartman

(57) ABSTRACT

A heel-supporting boot capable of supporting a leg of a person in a supine reclining position, such as a bedridden patient, to reduce the risk of bed sores, foot drop, etc. The boot includes a flexible and compressible body having leg and forefoot portions, a continuous cavity within the leg and forefoot portions, an anterior opening to permit a patient's foot and leg to pass therethrough into the cavity, oppositely-disposed lateral regions defined by the leg portion and separated by the anterior opening, and an adjustable closing feature for closing the anterior opening with the lateral regions. A stitch pattern is disposed along at least the forefoot rim, and preferably also the lateral rims, bounding the anterior opening. The stitch pattern is sufficiently close to the forefoot rim and optionally the lateral rims to structurally reinforce the forefoot rim and inhibit elastic and plastic deformation of the forefoot portion.

20 Claims, 3 Drawing Sheets

HEEL-SUPPORTING PROTECTIVE BOOT

BACKGROUND OF THE INVENTION

The present invention generally relates to devices adapted to support a leg of a person while reclining, especially patients that are bedridden and as a result are prone to bed sores, foot drop (equinus deformity foot-ankle), and other conditions that can affect the foot. More particularly, the invention is directed to a protective boot adapted to support a patient's leg at a location away from the heel such that the heel is suspended and yet the foot is properly supported, and the construction of such a boot to improve its support capabilities.

Bedridden patients can suffer from a variety of conditions brought on by being confined in bed, especially if limited to the supine position. For example, bedridden patients are susceptible to heel pressure ulcers, foot drop caused by relaxation and weakening of the muscles controlling the foot, and heel cord contracture. As a preventive measure, various foot support devices have been proposed, notable examples of which are disclosed in U.S. Pat. No. 4,186,738 to Schleicher et al. and U.S. Pat. No. 5,449,339 to Drennan. The latter patent discloses a heel-supporting boot commercially available from DM Systems Inc. under the name HEELIFT® Suspension Boot. The boot includes a unitary body formed of a flexible and compressible foam material that defines a foot supporting portion and a leg supporting portion. The leg supporting portion is configured to wrap around the leg of a patient away from the patient's foot, and is equipped with adjustable straps that secure the boot in place on the patient's leg to inhibit movement of the boot out of a proper supportive position in the event the patient moves. The leg supporting portion supports the patient's leg from beneath to suspend the patient's foot above the surface on which the patient is reclined, with the result that heel ulcers are prevented. The foot supporting portion supports the foot by applying pressure to the sole, thereby preventing foot drop, heel cord contracture, etc. The lower surface of the boot is provided with a friction-reducing element that promotes free sliding movement of the boot over the bed surface, and a stiffener is provided within the boot body to inhibit buckling and folding of the boot due to friction with the bed surface. The current commercial embodiment of the HEELIFT® boot is formed of soft polyurethane foam approximately 1.5 inches (about 4 cm) thick. To reduce tearing of the foam, a double row of stitching is provided along the edges of two arcuate junctions that interconnect the foot and leg portions.

While successful in achieving the above-noted functions, further improvements to foot-supporting boots would be desirable, particularly with respect to durability and strength to enhance and extend the protection offered by the boot against foot drop. Improvements in the ease with which the boot is secured to the foot and lower leg would also be desirable.

BRIEF SUMMARY OF THE INVENTION

The present invention provides a boot capable of supporting the lower leg of a person in a supine reclining position, as is often the case with bedridden patients, such that the risk of heel sores, foot drop, and other foot conditions are avoided. The boot of this invention is configured to provide proper support over extended periods of time as a result of exhibiting enhanced durability and strength in certain regions of the boot. The boot is also preferably configured to promote the ease with which the boot is positioned and secured.

The heel-supporting boot of this invention includes a body formed of a flexible and compressible material having a leg portion, a forefoot portion contiguous with and projecting from the leg portion in a transverse direction thereto, a continuous cavity defined by and within the forefoot and leg portions, an anterior opening defined in the forefoot and leg portions to permit a patient's foot and leg to pass therethrough into the cavity, and oppositely-disposed lateral regions defined by the leg portion and separated by the anterior opening. The anterior opening is bounded by lateral rims defined by the lateral regions and a forefoot rim defined by the forefoot portion. The cavity within the leg and forefoot portions is complementary in size and shape so that the leg portion supports the patient's leg, the heel of the patient's foot is suspended within the cavity to reduce heel pressure, and the forefoot portion supports the patient's foot in an upright position to prevent foot drop. The boot further includes an adjustable closing feature for closing the anterior opening with the lateral regions of the leg portion. Finally, a stitch pattern is disposed along at least the forefoot rim bounding the anterior opening, and preferably also along the lateral rims. The stitch pattern is sufficiently close to the forefoot rim and optionally the lateral rims to structurally reinforce the forefoot rim and inhibit elastic and plastic deformation of the forefoot portion.

A significant advantage of the invention as described above is that the forefoot portion is able to provide more complete protection against foot drop as a result of the stitch pattern being able to offset the tendency for the resilience of the flexible, compressible material of the body to weaken and allow the patient's forefoot to sag into plantar flexion, which might otherwise lead to the development of mild heel cord contracture over time. The stitch pattern also inhibits flaring or flattening of the forefoot portion of the boot, which if unchecked can create a broad bulky area causing patient discomfort, interference with movement of the patient, and increased friction with bed sheets.

In a preferred embodiment of the invention, the boot is equipped with a posterior stiffener and low friction covering, such as in accordance with U.S. Pat. No. 5,449,339 to Drennan. The present invention cooperates with and improves over the performance of these features, especially in circumstances where these features cannot protect against buckling and folding of the boot resulting from friction with bed sheets. For example, if the patient were to flex the ipsilateral knee and push down and forward, or draw back firmly against the sheets, thereby causing the unprotected forefoot portion susceptible to catching on the bed sheets, the stitch pattern helps maintain the shape of the forefoot portion of the boot to prevent buckling of the forefoot portion and displacement of the patient's foot from the boot.

Also in the preferred embodiment of the invention, the adjustable closing feature is configured to comprise individual straps, each of which wraps around the leg portion of the boot and is secured with the assistance a buckle that simplifies tightening and adjustment of the strap.

Other objects and advantages of this invention will be better appreciated from the following detailed description.

DETAILED DESCRIPTION OF THE INVENTION

Figure 1:
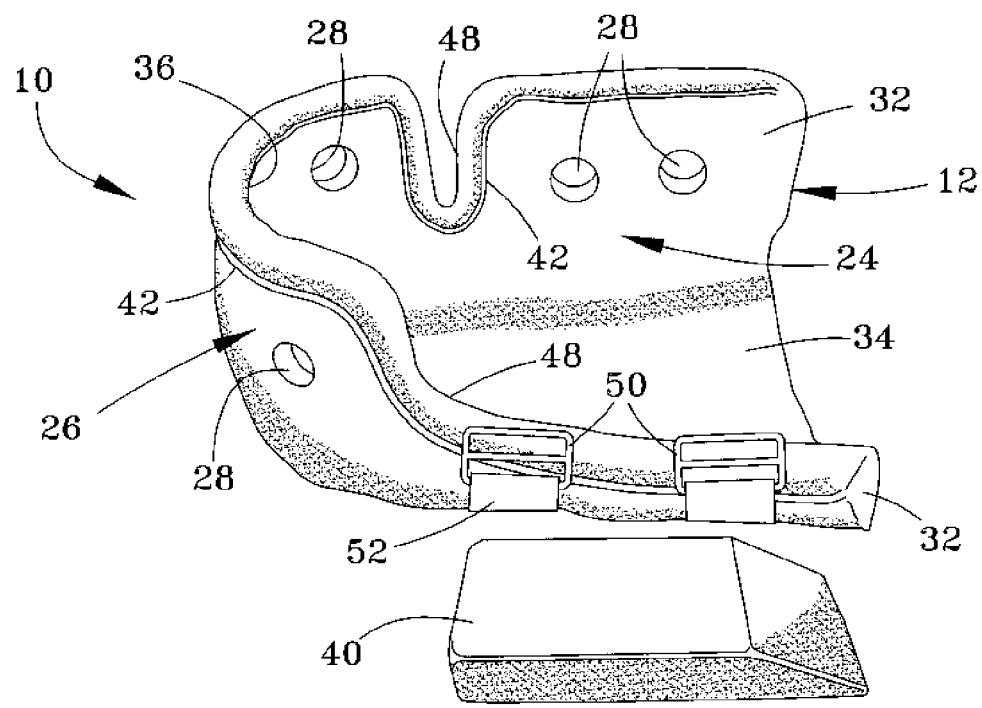
FIG. 1 is a perspective view of a heel-supporting boot in accordance with a preferred embodiment of this invention.

FIGS. 1 through 5 represent a boot 10 configured to be worn on a patient's foot 14 and lower leg 16 while the patient is in a generally supine position (reclining) on a bed 58 (or any other surface on which a person might recline while wearing the boot 10). The boot 10 is configured to support the patient's heel 18 in a manner that avoids foot drop and relieves heel pressure to avoid heel pressure ulcers. The boot 10 is believed to be an improvement over the function and construction of a suspension boot commercially available under the name DM Systems HEELIFT®, disclosed in U.S. Pat. No. 5,449,339 to Drennan, of which the contents relating to the construction and composition of the suspension boot are incorporated herein by reference.

Figure 4:
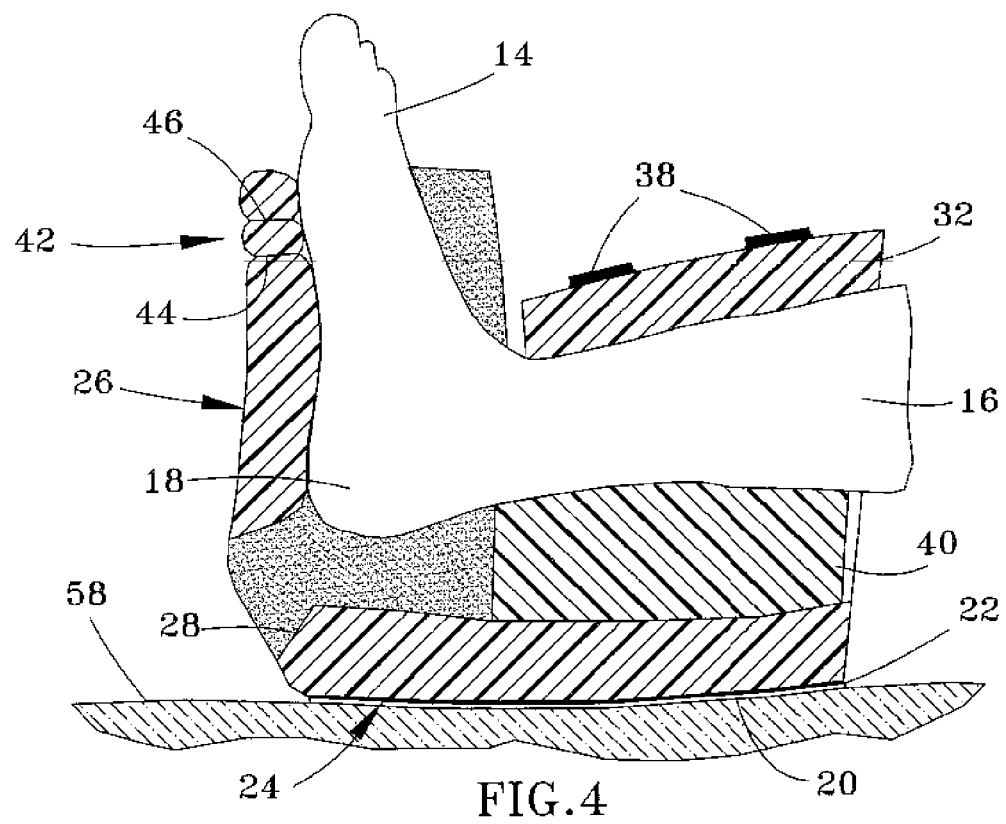
FIG. 4 represents a sectional view of FIG. 3.

As represented in FIG. 4, and consistent with the HEELIFT® boot, the boot 10 of this invention is adapted to support the lower leg 16 and foot 14 of a patient with a soft foam shell 12 secured to the lower leg 16 with straps 38. The shell 12 has a leg portion 24 that supports the lower leg 16 and elevates the foot 14, and a forefoot portion 26 that supports the foot 14 by applying supportive pressure to the sole. Because the boot 10 of this invention is similarly constructed and configured in accordance with Drennan, it shares the same advantages and benefits. The boot 10 of this invention improves over the teachings of Drennan by having a construction that stiffens and improves the life of the boot 10, particularly in the region of the forefoot portion 26 where loss of strength and shape can lead to foot drop and other conditions of the foot 14 and lower leg 16. In the preferred embodiment, the straps 38 with which the boot 10 is secured to the lower leg 16 are configured to greatly simplify tightening and adjustment of the boot 10.

Figure 2:
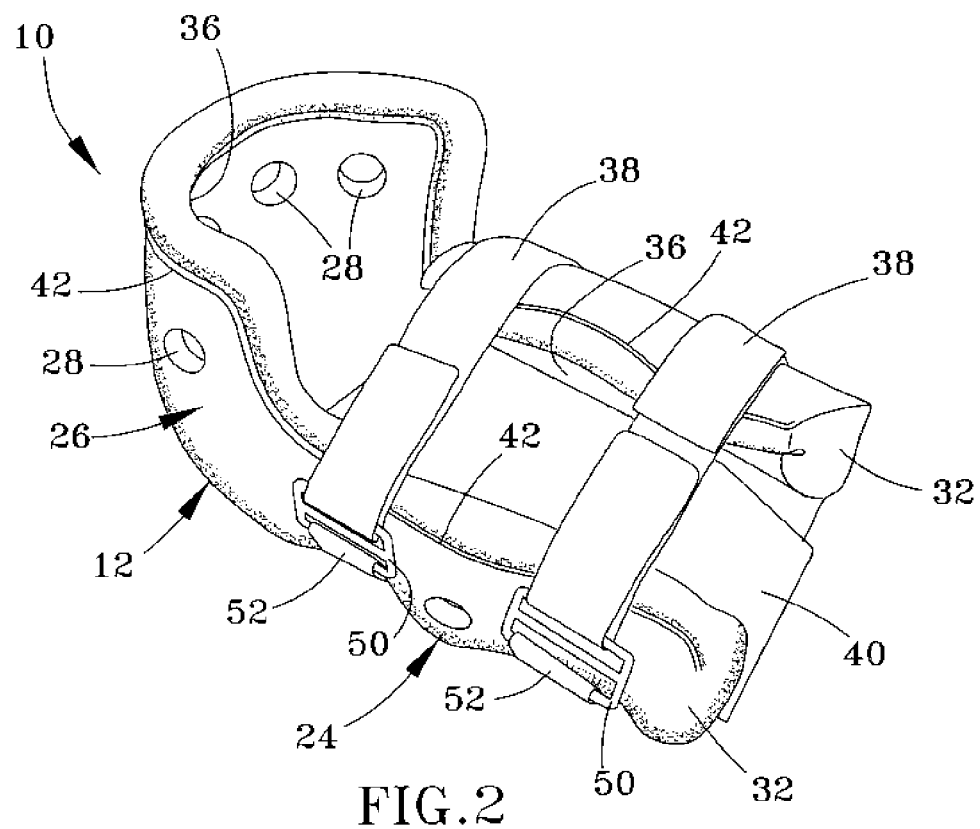
FIG. 2 is a perspective views of the boot of FIG. 1 with a leg portion of the boot closed.
Figure 3:
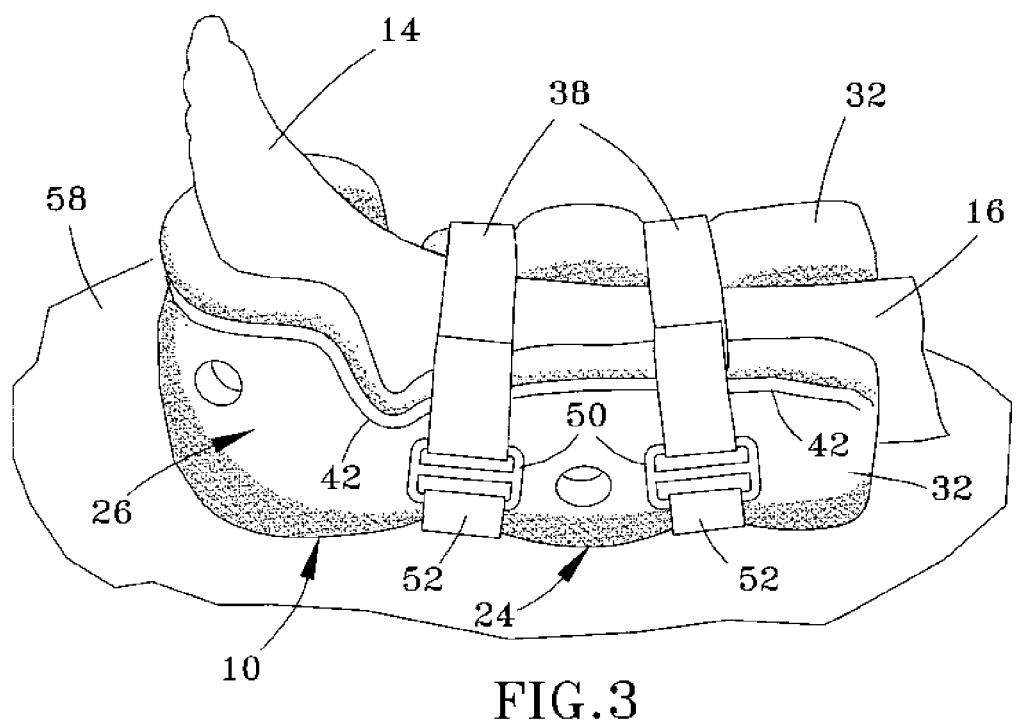
FIG. 3 depicts the boot of FIGS. 1 and 2 as it appears when worn on the lower leg of a patient.

With reference now to FIGS. 1 through 4, the shell 12 can be generally described as having oppositely-disposed anterior and posterior regions, with these terms being used in reference to the orientation of the boot 10 when worn by a person as shown in FIGS. 3 and 4. The leg portion 24 defines oppositely-disposed lateral regions 32, and together the leg and forefoot portions 24 and 26 define a continuous cavity 34 sized and shaped to receive the foot and lower leg 14 and 16 as shown in FIG. 4. An anterior opening 36 is defined by and between the lateral regions 32, and is sized to permit the patient's foot 14 and lower leg 16 to be lowered therethrough into the cavity 34, as evident from FIG. 1. In FIGS. 1 through 3, the righthand lateral region 32 of the shell 12 can be seen as being sized larger than the lefthand region 32 to cover at least an anterior portion of the patient's lower leg 16, as evident from FIGS. 3 and 4. The shell 12 is secured to the lower leg 16 with the straps 38 that traverse the anterior opening 36.

The boot 10 further comprises a separable cushion 40 that can be placed within the shell cavity 34 as shown in FIGS. 2 and 4 to further elevate the lower leg 16 (calf), thereby supporting the foot 14 and lower leg 16 without applying any support pressure at the heel 18 to avoid pressure sores at the heel 18. A suitable material for the cushion 40 is a foam material, such as that described for the shell 12 below, though it is foreseeable that other materials could be used. The cushion 40 can be secured with an adhesive to the interior surface of the cavity 34 within the leg portion 24 of the boot 10. Alternatively, the cushion 40 could be releasably secured with, for example, complementary fasteners of the hook-and-loop type, to enable removal of the cushion 40 from the boot 10. The forefoot portion 26 contacts the sole of the foot 14 and provides sufficient support to the foot 14 to prevent foot-drop (and equinus contractures). In accordance with Drennan, the boot 10 may further comprise a separable pad (not shown) that can be placed within the cavity 34 between the forefoot portion 26 and the patient's foot 14 to provide additional support to the foot 14.

As can be seen in FIG. 4, the boot 10 may include a low-friction backing 20 on its posterior surface to reduce friction with bed sheets, which would have the effect of interfering with movement of the patient and repositioning of the boot 10. The low-friction backing 20 preferably overlies a stiffener 22 on the posterior surface of the leg portion 24 to minimize buckling of the boot 10 within the leg and forefoot portions 24 and 26. Both the backing 20 and stiffener 22 can be held in place with stitching (not shown). As reported in Drennan, suitable materials for the low-friction backing 20 and stiffener 22 include a tricot material and polyethylene, respectively, though other materials could foreseeably be used. The boot 10 may further be equipped with accessory pads (not shown) that can be placed externally adjacent the lateral regions 32 of the boot 10 to control external rotation of the boot 10. As with the pad 40 within the boot cavity 34, these accessory pads can be releasably attached to the lateral regions 32 with adhesive, hook-and-loop fasteners, etc.

The shell 12 is preferably a unitary body formed of a flexible, compressible foam material. A particularly preferred shell 12 is formed from a slab of open-cell non-allergenic resilient foam material such as polyurethane foam, with sufficient thickness (e.g., about 1.5 inches (about 4 cm)) to elevate the patient's foot 14 and lower leg 16 above the bed (FIG. 4) and provide sufficient structural support to inhibit movement of the foot 14 and lower leg 16. The leg and forefoot portions 24 and 26 of the shell 12 are preferably formed to have ventilation holes 28 that help to improve the comfort of the patient when the boot 10 is worn for long periods, though these holes 28 could be eliminated for some applications. Because of its foam construction, the shell 12 has a soft foam interior surface that provides a high friction interface with the patient's skin. As depicted in the Figures, the interior surface of the shell 12 is smooth, though alternatively the surface could be convoluted, having a pattern of peaks and valleys as shown in Drennan. Commercially available foam materials having this type of surface are known as convoluted foam or egg carton foam. In combination with the adjustable straps 38 (described in greater detail below), the soft foam interior surface is able to prevent sliding of the lower leg 16 within the boot 10.

Figure 5:
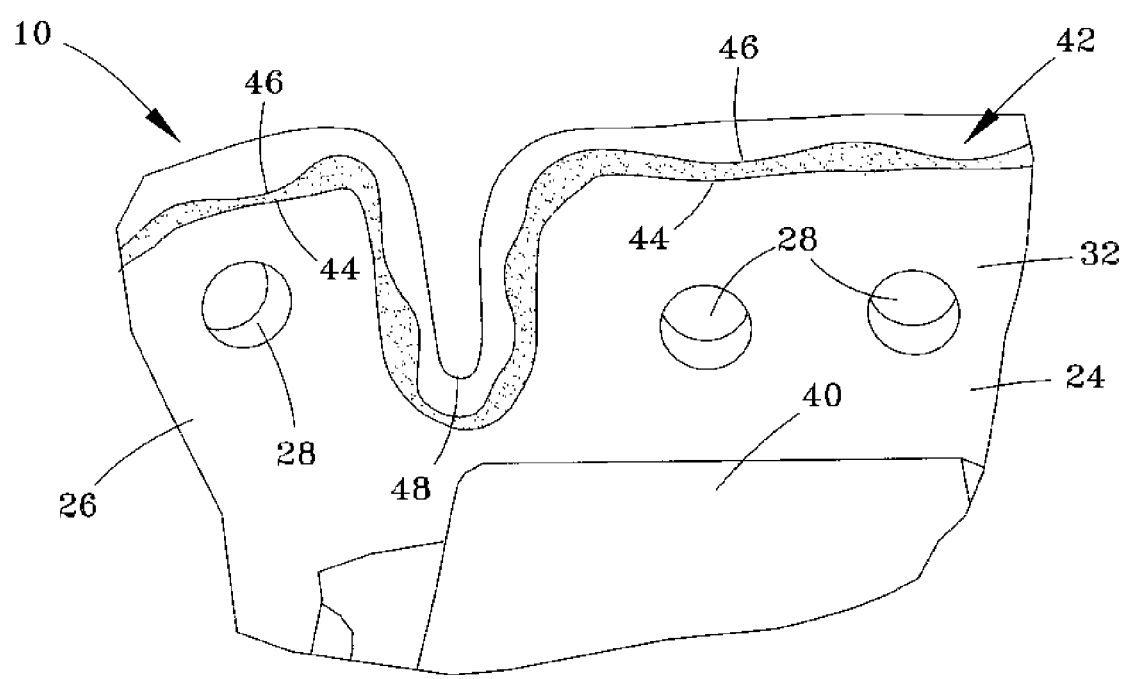
FIG. 5 is a detailed view of a portion of the boot of FIGS. 1 through 4.

As evident from FIGS. 1 through 5, the boot 10 of this invention further includes a multi-row stitch pattern 42 along the edge of the shell 12 defined by the anterior opening 36. As best seen in FIG. 5, the stitch pattern 42 is preferably formed by a pair of stitches 44 and 46, though it is foreseeable that more than two stitches could be employed. FIG. 1 shows the stitch pattern 42 as running from the proximal top rim of the righthand lateral region 32 of the leg portion 24, forward (distally) toward the forefoot portion 24, and then down (posteriorly) into a cleft-shaped junction 48 of the leg and forefoot portions 24 and 26 of the boot 10. The stitch pattern 42 then passes upward (anteriorly) along a relatively straight edge of the forefoot portion 24 to an arcuate rim of the forefoot portion 24, which as represented in the Figures lies substantially in a plane normal to the anterior-posterior direction of the boot 10. The stitch pattern 42 then passes downward (posteriorly) along a second relatively straight edge of the forefoot portion 24, through a second junction 48 of the leg and forefoot portions 24 and 26, and then proximally along the rim of the lefthand lateral region 32 of the leg portion 24.

The presence of the continuous stitch pattern 42 along the entire rim of the leg and forefoot portions 24 and 26, as defined by the anterior opening 36 of the shell 12, has been shown to limit elastic deformation of the forefoot portion 26 and thereby provide considerably more support to the patient's foot 14. When a patient plantar-flexes the foot 14, the double stitches 44 and 46 tense more than the foam shell 12 alone to bring the foot portion 26 of the boot 10 back to neutral faster and more firmly than possible with only the foam structure shell 12. In this manner, the boot 10 is more readily capable of preventing foot drop equinus and heel cord contracture. Because of their structural function, a preferred material for the stitches 44 and 46 is a non-elastic natural or synthetic woven thread, though a variety of other similarly durable materials could foreseeably be used including a polyester such as DACRON®.

As shown in better detail in FIG. 5, the stitches 44 and 46 preferably differ from each other. While the stitch 44 farthest from the shell rim is relatively at a constant distance from the rim, the stitch 46 closest to the rim is depicted as having a varying distance from the rim, preferably undulating and possibly approaching a sinusoidal shape. As evident from FIG. 4, in combination the stitches 44 and 46 narrow and compress the rim of the boot 10. For example, the stitches 44 and 46 can reduce the standard 1.5 inch (about 4 cm) thick foam rim of the HEELIFT® boot to a rounded 3/8 inch (about 1 cm) wide beadlike rim. In addition to the strengthening effect, this aspect of the invention also has the advantage of reducing the width of the forefoot portion 26, which reduces the likelihood of catching the forefoot portion 26 on sheets or other obstacles while moving the patient. The presence of the continuous stitch pattern 42 along the arcuate rim of the forefoot portion 26 also pulls the corners of the forefoot portion 26 laterally inward around the foot 14, with the result that foot pressure applied by the patient to the forefoot portion 26 causes further collapsing of the forefoot portion 26 around the foot 14 to increase support. This aspect of the invention could be promoted by adding a strap (not shown) adapted to surround the forefoot portion 26 to hold it closer and more firmly to the foot 14.

The presence of the continuous stitch pattern 42 along the rims of the lateral regions 32 of the boot 10 is also advantageous in circumstances such as when the patient flexes the ipsilateral knee and pushes down (posteriorly) hard. In this situation, the forefoot portion 26 is not protected from friction with the bed sheets by the low friction backing 20 or stiffener 22, raising the possibility that some buckling of the forefoot portion 26 could occur, potentially allowing the heel 18 to slide forward and out of the boot 10. The continuous stitches 44 and 46 extending along the entire lengths of the rims of the lateral regions 32 to and into the forefoot portion 26 behave as a tether to hold the forefoot portion 26 up and back to limit the possibility of displacement of the foot 14 from the boot 10 and the subsequent need to reposition the boot 10.

By limiting elastic deformation of the shell 12, the continuous stitch pattern 42 of this invention also inhibits plastic deformation of the shell 12, particularly in the region of the forefoot portion 26. For example, the stitch pattern 42 is able to offset the tendency for the resilience of the flexible, compressible material of the shell 12 to weaken and allow the patient's foot 14 to sag into plantar flexion. The stitch pattern 42 also inhibits flaring or flattening of the forefoot portion 26 of the boot 110, which if unchecked can create a broad bulky area that causes patient discomfort, interferes with movement of the patient, increases friction with bed sheets, etc. The presence of the stitch pattern 42 also has the structural advantage of reducing stress risers created by the air ventilation holes 28 within the leg and forefoot portions 24 and 26 of the boot 10, thereby reducing the incidence of tearing if the patient is hyperactive or spastic. Finally, it should be noted that the stitches 44 and 46 are recessed below the predominant surface of the cavity 34 and almost buried within the soft foam of the shell 12, such that the stitches 44 and 46 do not cause focal pressure on the foot 14 that could lead to sores or ulceration.

As noted above, the preferred embodiment of the boot 10 shown in the Figures also incorporates a strap system that facilitates tightening and adjustment of the boot 10 on the patient's lower leg 16. More particularly, the boot 10 preferably makes use of two straps 38, each working in cooperation with a buckle 50 attached to one of the lateral regions 32 of the leg portion 24. Each strap 38 may be attached to the lateral region 32 opposite the buckles 50 (e.g., the righthand lateral region 32 in the Figures), or optionally attached on the same lateral region 32 near the attachment point of its corresponding buckle 50 (e.g., the lefthand lateral region 32 in the Figures). In use, the straps 38 are passed over the anterior opening 36 of the shell 12 toward their respective buckles 50, as seen in FIGS. 2 and 3. The buckles 50 provide a generally D-shaped ring or slot through which the straps 38 can be inserted and then drawn back on themselves, allowing each strap 38 to be secured to itself with a suitable fastener, such as a complementary hook and loop closure material. As depicted in the Figures, the buckles 50 are preferably attached to the smaller lateral region 32 located on the left side of the boot 10, so that the larger lateral region 32 on the right side of the boot 10 is drawn down over the leg 16 as the straps 38 are passed over the anterior opening 36 toward the buckles 50. By inserting the straps 38 in the buckles 50 and then drawing the straps 38 back onto themselves, the larger lateral region 32 is drawn snug over the patient's lower leg 16, as can be appreciated from FIGS. 3 and 4. The strength of the attachment of the buckles 50 to the shell 12 can be promoted by attaching the buckles 50 with straps 52 that can be held with the same stitching lines (not shown) that hold the low friction backing 20 and stabilizer 22 in place within the leg portion 24. The attachment of the buckles 50 with the short straps 52 is believed to be preferable over rigidly attaching the buckles 50 to the shell 12 to allow some mobility of the buckles 50 for easier use and avoid the possibility of a rigid connection causing pressure and discomfort to the patient.

The strap system of this invention is believed to have several advantages over the strap system of Drennan. The buckles 50 serve as fulcrums for the straps 38, allowing the patient or a caregiver to insert and properly tension each strap 38 with a single hand. This aspect frees up the second hand of the patient, which can then be used to balance the patient in bed while inserting or adjusting the straps 38. If a caregiver is performing this task, one hand of the caregiver is free to position and stabilize the patient's leg 16 and foot 14 within the boot 10. In either scenario, a proper amount of tension can be applied with the straps 38 with one hand while also ensuring proper positioning of the leg 16 within the boot 10.

While the invention has been described in terms of a preferred embodiment, it is apparent that other forms could be adopted by one skilled in the art. For example, the physical configuration of the boot 10 could differ from that shown, and materials other than those noted could be use. Therefore, the scope of the invention is to be limited only by the following claims.

What is claimed is:

1. A heel-supporting boot for a person lying in a supine position, the boot comprising:

a body formed of a flexible and compressible foam material having a leg portion, a forefoot portion contiguous with and projecting from the leg portion in a transverse direction thereto, a continuous cavity defined by and within the leg and forefoot portions, an anterior opening defined in the leg and forefoot portions to permit a patient's foot and lower leg to pass therethrough into the cavity, and oppositely-disposed lateral regions defined by the leg portion and separated by the anterior opening, the anterior opening being bounded by lateral rims defined by the lateral regions and a forefoot rim defined by the forefoot portion, the cavity within the lower leg and forefoot portions being complementary in size and shape so that the leg portion supports the patient's lower leg, the heel of the patient's foot is suspended within the cavity to reduce heel pressure, and the forefoot portion supports the patient's foot in an upright position to prevent foot drop;

means for adjustably closing a portion of the anterior opening in the leg potion with the lateral regions of the leg portion; and a stitch pattern comprising at least a first stitch disposed along substantially the entire forefoot rim bounding the anterior opening, the stitch pattern thickness-wise narrowing and compressing the foam material along the forefoot rim so that the first stitch is recessed in opposite surfaces of the foam material, the stitch pattern being sufficiently close to the forefoot rim to structurally reinforce the forefoot rim and inhibit elastic and plastic deformation of the forefoot portion.

2. The heel-supporting boot according to claim 1, wherein the first stitch is spaced a substantially constant distance from the forefoot rim.

3. The heel-supporting boot according to claim 2, wherein the stitch pattern further comprises a second stitch that is spaced a nonconstant distance from the forefoot rim.

4. The heel-supporting boot according to claim 3, wherein the second stitch has a substantially undulating shape.

5. The heel-supporting boot according to claim 3, wherein the second stitch is closer to the forefoot rim than the first stitch.

6. The heel-supporting boot according to claim 3, wherein the first and second stitches are each continuous along the forefoot rim.

7. The heel-supporting boot according to claim 1, wherein the at least one stitch is spaced a nonconstant distance from the forefoot rim.

8. The heel-supporting boot according to claim 1, wherein the stitch pattern is continuous along the forefoot rim.

9. The heel-supporting boot according to claim 1, wherein the stitch pattern is also disposed along substantially the entire lateral rims bounding the anterior opening.

10. The heel-supporting boot according to claim 1, wherein the forefoot rim comprises an arcuate rim portion substantially in a plane normal to the transverse direction of the forefoot portion and a pair of linear rim portions substantially parallel to the transverse direction of the forefoot portion and interconnecting the arcuate rim portion with the lateral rims.

11. The heel-supporting boot according to claim 10, wherein the stitch pattern is continuous along the arcuate rim portion and the pair of linear rim portions so as to inhibit flexing of the forefoot portion relative to the leg portion.

12. The heel-supporting boot according to claim 1, wherein the closing means comprises straps attached to the leg portion, a buckle associated with each of the straps, and fastening means on the straps, and each of the straps is attached to one of the lateral regions and is sufficiently long to traverse the anterior opening, pass through the buckle associated therewith, and overlap itself so that the fastening means secures the strap to itself.

13. The heel-supporting boot according to claim 12, wherein one of the lateral regions of the body is larger than the other of the lateral regions and is sufficiently sized to close the anterior opening within the leg portion when the anterior opening is closed by the closing means.

14. The heel-supporting boot according to claim 1, further comprising means for reducing friction on a posterior region of the body opposite the anterior opening to promote sliding movement of the body on the bed on which the patient reclines.

15. The heel-supporting boot according to claim 1, further comprising means for stiffening a posterior region of the body opposite the anterior opening to inhibit buckling of the body between the leg and forefoot portions thereof.

16. The heel-supporting boot according to claim 1, further comprising a separate support cushion within the cavity of the body, the support cushion being located within the leg portion of the body for supporting the patient's lower leg within the cavity and suspending the patient's heel within the cavity.

17. The heel-supporting boot according to claim 16, wherein the support cushion is formed of a flexible and compressible material.

18. The heel-supporting boot according to claim 17, wherein the support cushion is secured to a surface of the cavity within the leg portion of the body.

19. A heel-supporting boot for a person lying in a supine position, the boot comprising:

a body formed of a flexible and compressible foam material having a leg portion, a forefoot portion contiguous with and projecting from the leg portion in a transverse direction thereto, a continuous cavity defined by and within the leg and forefoot portions, an anterior opening defined in the leg and forefoot portions to permit a patient's foot and lower leg to pass therethrough into the cavity, and oppositely-disposed lateral regions defined by the leg portion and separated by the anterior opening, the anterior opening being bounded by lateral rims defined by the lateral regions and a forefoot rim defined by the forefoot portion, the cavity within the lower leg and forefoot portions being complementary in size and shape so that the leg portion supports the patient's lower leg above a bed on which the patient reclines, the heel of the patient's foot is suspended within the cavity to reduce heel pressure, and the forefoot portion supports the patient's foot in an upright position to prevent foot drop;

means for adjustably closing a portion of the anterior opening in the leg potion with the lateral regions of the leg portion, the closing means comprising straps attached to the leg portion, a buckle associated with each of the straps, and fastening means on the straps, each of the straps being attached to one of the lateral regions and sufficiently long to traverse the anterior opening, pass through the buckle associated therewith, and overlap itself so that the fastening means secures the strap to itself; and a stitch pattern comprising multiple rows of stitches disposed along substantially the entire lateral rims and the entire forefoot rim bounding the anterior opening, the stitch pattern thickness-wise narrowing and compressing the foam material along the forefoot rim so that the stitches are recessed in opposite surfaces of the foam material, the stitch pattern being sufficiently close thereto to structurally reinforce the forefoot rim and inhibit plastic deformation of the forefoot portion, the stitches comprising a first stitch that is spaced a substantially constant distance from the forefoot rim and a second stitch that is closer to the lateral and forefoot rims than the first stitch and spaced a nonconstant distance from the forefoot rim.

20. The heel-supporting boot according to claim 19, wherein the forefoot rim comprises an arcuate rim portion substantially in a plane normal to the transverse direction of the forefoot portion and a pair of linear rim portions substantially parallel to the transverse direction of the forefoot portion and interconnecting the arcuate rim portion with the lateral rims, and the stitch pattern is continuous along the arcuate rim portion and the pair of linear rim portions so as to inhibit flexing of the forefoot portion relative to the leg portion.

* * * * *